(12) United States Patent
Miyake et al.

(10) Patent No.: US 9,207,162 B2
(45) Date of Patent: Dec. 8, 2015

(54) IMAGING APPARATUS

(71) Applicant: DAINIPPON SCREEN MFG. CO., LTD., Kyoto (JP)

(72) Inventors: Takashi Miyake, Kyoto (JP); Kunio Ikefuji, Kyoto (JP)

(73) Assignee: SCREEN Holdings Co., Ltd. (JP)

( * ) Notice: Subject to any disclaimer, the term of this patent is extended or adjusted under 35 U.S.C. 154(b) by 120 days.

(21) Appl. No.: 13/899,628

(22) Filed: May 22, 2013

(65) Prior Publication Data

US 2014/0051156 A1 Feb. 20, 2014

(30) Foreign Application Priority Data

Aug. 20, 2012 (JP) ................................. 2012-181526
Mar. 26, 2013 (JP) ................................. 2013-063863

(51) Int. Cl.
*G01N 21/01* (2006.01)
*A61L 2/10* (2006.01)
*G06K 9/00* (2006.01)

(52) U.S. Cl.
CPC . *G01N 21/01* (2013.01); *A61L 2/10* (2013.01); *G06K 9/00127* (2013.01)

(58) Field of Classification Search
CPC ....... G01N 21/01; A61L 2/10; G06K 9/00127
See application file for complete search history.

(56) References Cited

U.S. PATENT DOCUMENTS

| | | | |
|---|---|---|---|
| 6,151,161 A * | 11/2000 | Mayer et al. ................... | 359/392 |
| 6,462,771 B1 | 10/2002 | Kitagawa ....................... | 348/79 |
| 6,947,583 B2 | 9/2005 | Ellis et al. ...................... | 382/128 |
| 7,050,620 B2 | 5/2006 | Heckman ........................ | 382/133 |
| 7,120,282 B2 | 10/2006 | Langan ........................... | 382/128 |
| 7,129,473 B2 | 10/2006 | Ishihara et al. ................ | 250/234 |
| 7,190,818 B2 | 3/2007 | Ellis et al. ...................... | 382/128 |
| 7,262,858 B2 | 8/2007 | Lin et al. ........................ | 356/445 |
| 7,283,654 B2 | 10/2007 | McLain .......................... | 382/128 |
| 7,516,934 B2 | 4/2009 | Chu et al. ....................... | 248/550 |
| 7,582,415 B2 | 9/2009 | Straus .............................. | 435/4 |
| 7,718,131 B2 | 5/2010 | Jiang .......................... | 422/82.08 |
| 8,135,203 B2 | 3/2012 | Takagi et al. .................. | 382/133 |
| 2001/0053335 A1 | 12/2001 | Hashimoto et al. | |
| 2007/0242349 A1* | 10/2007 | Tafas ............................. | 359/391 |
| 2009/0086314 A1* | 4/2009 | Namba et al. ................. | 359/383 |
| 2009/0310839 A1 | 12/2009 | Katzenelson et al. | |
| 2010/0025567 A1 | 2/2010 | Luerssen ...................... | 250/205 |

FOREIGN PATENT DOCUMENTS

| | | |
|---|---|---|
| JP | 63-008537 A | 1/1988 |
| JP | 6-104075 B2 | 12/1994 |
| JP | 10-14560 A | 1/1998 |
| JP | 2000-275539 | 10/2000 |
| JP | 2006-000054 A | 1/2006 |
| JP | 2008-064534 | 3/2008 |

(Continued)

*Primary Examiner* — Regina M Yoo
(74) *Attorney, Agent, or Firm* — Ostrolenk Faber LLP

(57) ABSTRACT

An imaging apparatus, comprising a holder that holds a specimen container carrying a biological specimen, an imager that images the specimen in the specimen container, a sterilizer that supplies a drug or electromagnetic waves having a sterilization effect to the holder, and a controller that performs a sterilization process of supplying the drug or the electromagnetic waves to the holder by controlling the sterilizer at least either before or after imaging the specimen by the imager.

8 Claims, 11 Drawing Sheets

(56) References Cited

FOREIGN PATENT DOCUMENTS

| | | |
|---|---|---|
| JP | 2008-112190 | 5/2008 |
| JP | 2010-207278 A | 9/2010 |
| JP | 4584671 B2 | 11/2010 |
| JP | 2010-268723 | 12/2010 |
| WO | WO 02/37158 | 5/2002 |

* cited by examiner

F I G. 7
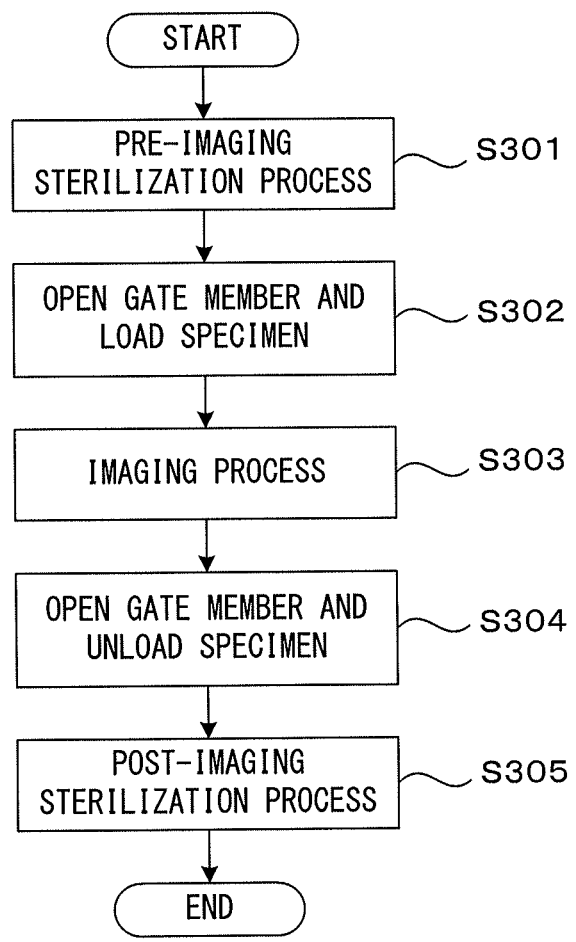

IMAGING APPARATUS

CROSS REFERENCE TO RELATED APPLICATION

The disclosure of Japanese Patent Applications enumerated below including specifications, drawings and claims is incorporated herein by reference in its entirety:
No. 2012-181526 filed on Aug. 20, 2012; and
No. 2013-063863 filed on Mar. 26, 2013.

BACKGROUND OF THE INVENTION

1. Field of the Invention

This invention relates to an imaging apparatus for imaging a biological specimen containing cells or the like.

2. Description of the Related Art

In medical or biological science experiments, sample tissues picked from a living organism or cells or the like cultured in a liquid or gel-like culture medium are, for example, observed and measured as a specimen. For this purpose, an analysis system configured by combining an imager for optically imaging a specimen to obtain an image and a calculator for analyzing the image obtained by the imager is proposed, for example, in JP2000-275539A.

In an imaging apparatus for imaging an image used for this kind of purpose, imaging while replacing a plurality of specimens of different types, culture conditions and the like one after another, time lapse imaging of imaging a growth process of cells in one specimen at time intervals a plurality of times, and the like are performed.

In imaging a biological specimen as described above, the specimen may be affected by an environment in which the specimen is placed during imaging. For example, contamination-causing substances such as bacteria or spores of fungi having entered the imaging apparatus from outside, substances separated from a specimen used for the previous imaging and the like may be mixed into the specimen to contaminate the cells and the like contained in the specimen.

The apparatus has been conventionally manually sterilized by an operator. There have been cases where the above cause of contamination cannot be said to be sufficiently eliminated mainly due to a human error such as remaining contamination-causing substances caused by an error in an operation procedure or inconsistency in operation or the omission of a sterilization operation itself.

SUMMARY OF THE INVENTION

This invention was developed in view of the above problem and aims to provide a technology capable of reliably preventing the contamination of a specimen as an imaging object by bacteria or the like in an imaging apparatus for imaging a biological specimen and obtaining an image thereof.

One aspect of this invention is directed to an imaging apparatus, comprising a holder for holding a specimen container carrying a biological specimen, an imager for imaging the specimen in the specimen container, a sterilizer for supplying a drug or electromagnetic waves having a sterilization effect to the holder, and a controller for performing a sterilization process of supplying the drug or the electromagnetic waves to the holder by controlling the sterilizer at least either before or after imaging the specimen by the imager.

In the invention thus configured, the sterilization process is performed by supplying the drug or the electromagnetic waves having the sterilization effect from the sterilizer to the holder in accordance with a control of the controller. This enables an execution timing of the sterilization process and the content of that process to be properly managed and prevents a flaw in the sterilization process due to inconsistency in operation, improper operation or the like by an operator. Thus, in the invention, the holder can be more reliably and stably sterilized and the contamination of the specimen in the specimen container held by the holder by bacteria or the like can be reliably prevented.

According to this invention, it is possible to properly manage the execution timing of the sterilization process and the content of that process and prevent a flaw in the sterilization process due to inconsistency in operation, improper operation or the like by an operator. Thus, the holder can be more reliably and stably sterilized and the contamination of the specimen in the specimen container held by the holder by bacteria or the like can be reliably prevented.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

BRIEF DESCRIPTION OF THE DRAWINGS

FIG. 7 is a flow chart which shows the flow of the imaging process in the third embodiment.

DETAILED DESCRIPTION OF THE PREFERRED EMBODIMENTS

First Embodiment

Figure 1:
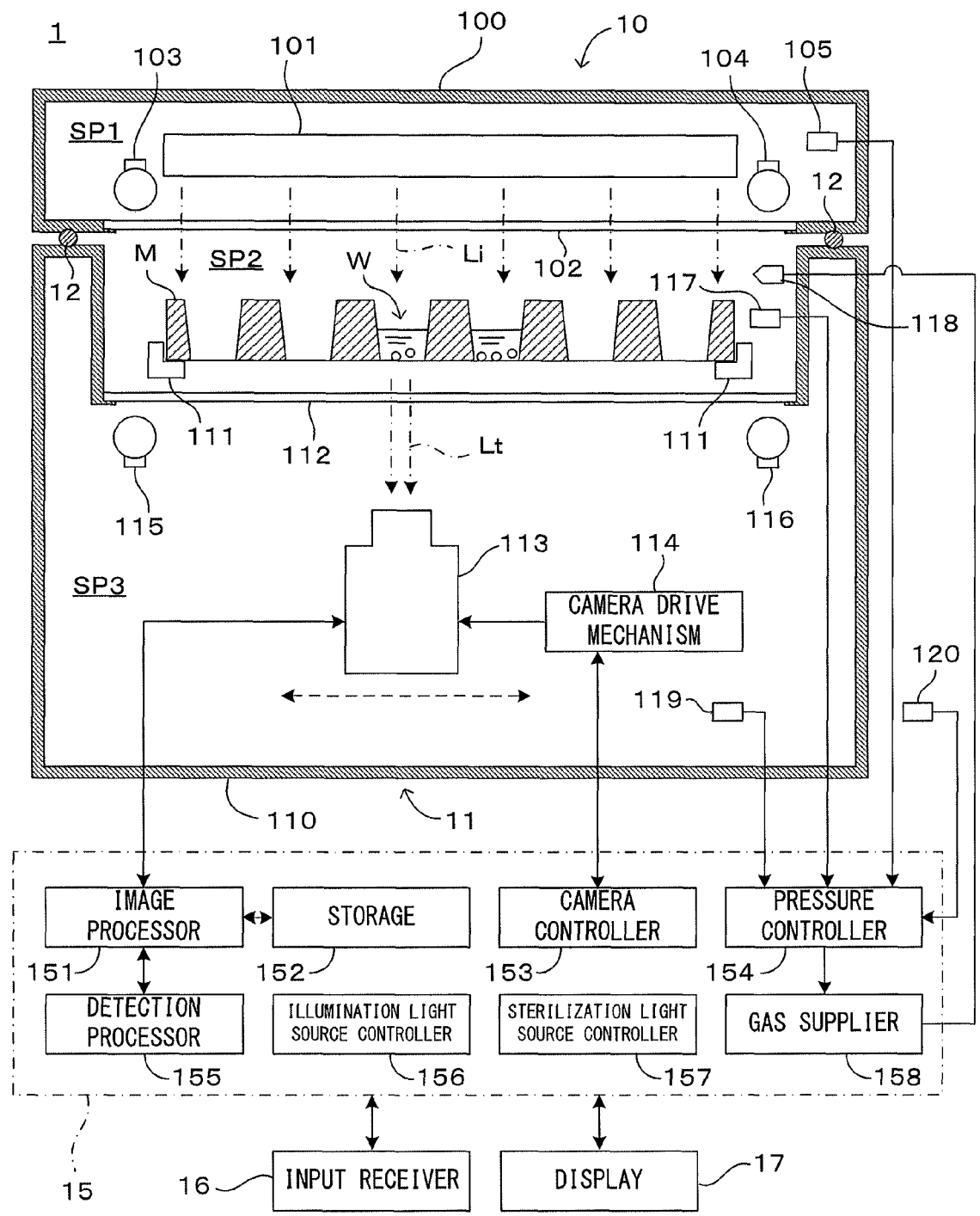
FIG. 1 is a diagram which shows a schematic configuration of an imaging apparatus according to a first embodiment of the invention.

FIG. 1 is a diagram which shows a schematic configuration of an imaging apparatus according to a first embodiment of the invention. More specifically, FIG. 1 shows a side sectional view of a main part of an imaging apparatus 1 of the first embodiment and is a block diagram of the configuration of a control unit. This imaging apparatus 1 is, for example, used to image an image used for the analysis of biological specimens such as cells and body tissues cultured in wells W of a microplate M to be described later. The imaging apparatus 1 optically reads specimens and performs a predetermined calculation on image data obtained by the reading. The imaging apparatus 1 includes an illumination unit 10 which illuminates specimens, an imaging unit 11 which houses specimens and a camera 113 and a control unit 15 which performs an imaging process by controlling respective parts of the apparatus.

The illumination unit 10 is so structured that in an internal space SP1 of a chamber 100, an illumination light source 101 for emitting light (visible light, e.g. white light) for illuminating specimens, sterilization light sources 103, 104 for emitting light having a sterilization effect, e.g. UV light (ultraviolet rays) and an air pressure sensor 105 for measuring an air pressure in the internal space SP1 are housed. A transparent window 102 which is transparent to the illumination and sterilization light (e.g. visible light and UV light) is provided on the bottom surface of the chamber 100. On the other hand, chamber wall surfaces excluding the bottom surface are made of a material which is opaque at least to UV light. This material is more preferably a material having high reflectance to UV light. The visible light emitted from the illumination light source 101 and the UV light emitted from the sterilization light sources 103, 104 are irradiated downward through the transparent window 102.

The imaging unit 11 includes a chamber 110, a central part of the upper surface of which is recessed downward to have a bathtub shape. This central part of the upper surface serves as a transparent window 112 which is transparent to the illumination and sterilization light, and the transparent window 112 also functions as a partition wall which partitions the interior of the chamber 110 into an upper space SP2 and a lower space SP3.

The illumination unit 10 is mounted to cover an upper part of the chamber 110, and the upper space SP2 of the chamber 110 is closed and opened by bringing the illumination unit 10 into and out of contact with the chamber 110. Specifically, the upper space SP2 of the chamber 110 serves as a sealed space by mounting the illumination unit 10 on the top of the chamber 110 via a packing 12. The microplate M holding specimens as imaging objects is disposed in this sealed space and an imaging process is performed. That is, the upper space SP2 of the chamber 110 functions as a specimen housing space, in which the specimens are housed during imaging, by closing the upper part of the upper space SP2 of the chamber 110 by the illumination unit 10. On the other hand, with the illumination unit 10 retracted upward, the upper space SP2 of the chamber 110 is open to outside space, thereby setting a state where the microplate M can be loaded and unloaded.

A holder 111 for holding the microplate M in a substantially horizontal posture is provided in the specimen housing space SP2. Besides this, an air pressure sensor 117 for measuring an air pressure in the specimen housing space SP2 and a gas discharge nozzle 118 for discharging predetermined gas into the specimen housing space SP2 are provided.

On the other hand, the camera 113 for imaging the specimens is housed in the lower space SP3 of the chamber 110. More specifically, the camera 113 and a camera drive mechanism 114 for moving and scanning the camera 13 in a horizontal direction (directions of broken-line arrows in FIG. 1) are provided in the lower space SP3.

Light Li emitted from the illumination light source 101 is irradiated downward to the microplate M through the transparent window 102 and incident on the specimens held in wells W. Transmission light Lt having transmitted through the microplate M downward is incident on the camera 113 through the transparent window 112. The camera 113 images an image of the microplate M by receiving the transmission light Lt being transmitted through the microplate M. The camera 113 is coupled to the camera drive mechanism 114, which moves and scans the camera 113 in a horizontal plane along the lower surface of the microplate M held by the holder 111. The camera 113 includes, for example, a line sensor as a light receiving element, and optically reads the microplate M from below to obtain a two-dimensional image of the microplate M by being moved and scanned in a direction intersecting with a longitudinal direction of the line sensor.

Specifically, in this imaging unit 11, the camera 113 can move and scan along the lower surface of the microplate M. Note that although the camera 113 moves relative to the microplate M here, it is sufficient to realize a relative movement between the camera 113 and the microplate M. In this sense, the microplate M may move relative to the camera 113.

Sterilization light sources 115, 116 for irradiating sterilization light, e.g. UV light toward the specimen housing space SP2 located above through the transparent window 112 and a pressure sensor 119 for measuring an air pressure in the lower space SP3 are further provided in the lower space SP3. Further, a pressure sensor 120 for measuring an atmospheric pressure outside the imaging apparatus 1 is provided outside the chamber 110.

Image data obtained by the camera 113 is fed to an image processor 151 provided in the control unit 15. The image processor 151 applies appropriate image processings such as noise removal and color separation to the image data from the camera 113. Data before and after the processings are saved and stored in a storage 152 according to needs. A detection processor 155 performs a predetermined detection process based on the thus processed image data.

A pressure controller 154 for respectively detecting air pressures in the respective spaces SP1, SP2 and SP3 and an atmospheric pressure based on output signals of the pressure sensors 105, 117, 119 and 120, and a gas supplier 158 for supplying gas to the gas discharge nozzle 118 in response to a control command from the pressure controller 154 are provided in the control unit 15. The pressure controller 154 controls the gas supplier 158 to set a state where the air pressure in the specimen housing space SP2 is slightly higher than in the other internal spaces SP1, SP2 and the outside space. Specifically, the air pressure in the specimen housing space SP2 is maintained in a state higher than the surrounding by releasing the gas supplied from the gas supplier 158 into the specimen housing space SP2 from the gas discharge nozzle 118. Preferably, the pressures in the upper space SP1 and the lower space SP3 are set to be slightly higher than the atmospheric pressure and the pressure in the specimen housing space SP2 is set to be highest. By applying a positive pressure relative to the air pressure in the surrounding space to the specimen housing space SP2, the entrance of contamination-causing substances such as fungi and bacteria into the specimen housing space SP2 from outside can be avoided.

Note that if this imaging apparatus 1 is installed in a room or a chamber where bacteria are cultured, a pressure in that room or chamber may be set to be different from an atmospheric pressure. For example, an indoor pressure may be set to be higher than an atmospheric pressure to reduce a risk of entrance of fungi and bacteria from outside. In such a case, the above pressure difference balance can be maintained by setting the pressures in the respective spaces according to the indoor pressure detected by the atmospheric pressure sensor 120.

Besides those described above, the control unit 15 includes a camera controller 153 for moving and scanning the camera 113 by controlling the camera drive mechanism 114, an illumination light source controller 156 for on/off controlling the illumination light source 101, a sterilization light source controller 157 for on/off controlling the sterilization light sources 103, 104, 115 and 116 and the like. These respective constituent elements control the respective parts of the apparatus while cooperating with each other, whereby various processing operations are realized. Note that these respective constituent elements may be realized either by hardware or by software.

Further, this imaging apparatus 1 includes an input receiver 16 for receiving the input of an operation instruction from a user and a display 17 for displaying a predetermined message to the user. Although not shown, the input receiver 16 includes an operation input device such as a keyboard, a touch panel or a group of operation buttons, and receives the input of an instruction from the user on the content of processings to be performed, parameter setting and the like. Further, the display 17 presents a processing menu, messages to the user associated with the progress of a process, and visual information such as imaged images at any time.

Figure 2A:
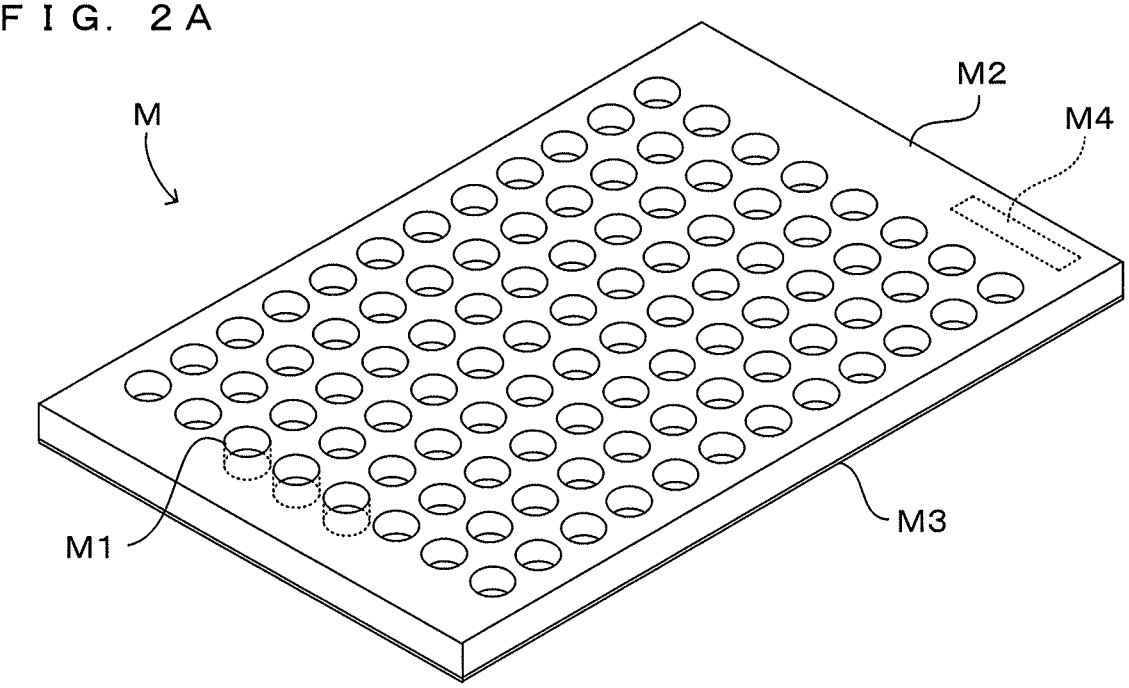
FIGS. 2A and 2B are drawings which show an example of the structure of the microplate.
Figure 2B:
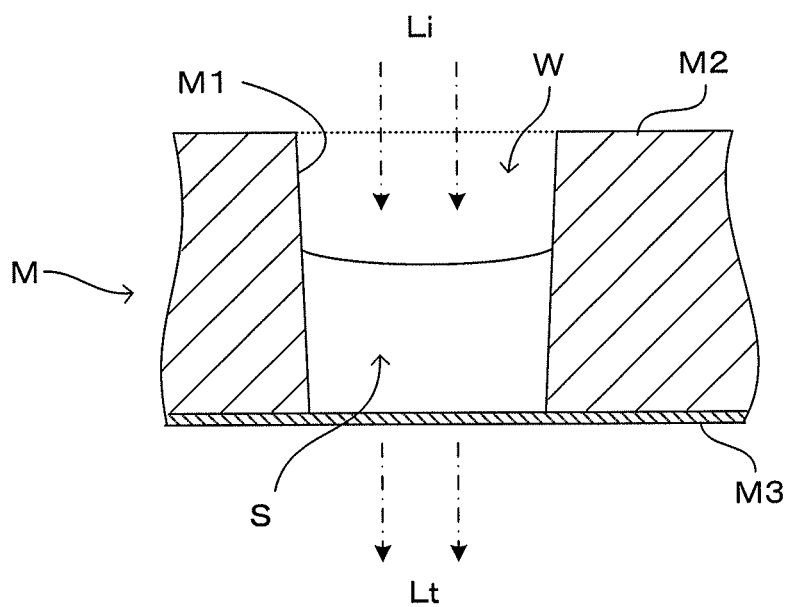

FIGS. 2A and 2B are drawings which show an example of the structure of the microplate. The microplate M is a plate-like equipment formed with a plurality of, e.g. 96 (12×8 matrix arrangement) recesses (wells) W on the upper surface. As shown in FIG. 2A, the microplate M includes an upper plate M2 in which through holes M1 having a substantially cylindrical (more strictly, tapered to gradually reduce a cross-sectional area toward the bottom surface) side surface shape are regularly arranged at constant intervals in a two-dimensional matrix and a lower surface sheet M3 attached to the lower surface of the upper plate M2 to close the respective through holes M1.

As shown in FIG. 2B, the lower surface sheet M3 is closely fitted to the lower surface of the upper plate M2 and liquid can be held in spaces enclosed by the side surfaces of the through holes M1 of the upper plate M2 and the lower surface sheet M3. Specifically, these spaces function as the wells W for holding culture media containing biological specimens, the side surfaces of the through holes M1 serve as side wall surfaces of the wells W and the lower surface sheet M3 serves as the bottom surfaces of the wells W. The lower surface sheet M3 is a sheet formed of transparent resin, e.g. PET (polyethylene terephthalate) resin.

The diameter and depth of each well W in the microplate M are typically about several mm. Liquid such as culture fluid, culture medium or reagent (only partly shown in FIG. 1) is injected in each well W. Note that the number and size of the wells of the microplate as an object of this imaging apparatus 1 are not limited to these and are arbitrary.

Culture media containing living tissues, cells or the like are injected into the thus formed wells W and cultured for a predetermined time in a constant temperature/humidity environment, whereby specimens S as imaging objects are prepared in the wells W. The microplate M is stored under a constant temperature/humidity environment until being imaged. When the microplate M is housed in the specimen housing space SP2 of the imaging apparatus 1, light emitted from the illumination light source 101 is incident as incident light Li from above the microplate M as shown in FIG. 2B. Then, the camera 113 receives transmission light Lt having transmitted through the specimens S in the wells W, whereby an image of the specimens S is obtained.

An attachment space M4 in which a recording medium such as a label, a bar code or a wireless communication tag recorded with information on the contents of the wells W, culture conditions and the like can be attached is provided on the upper, lower or side surface of the microplate M. The information recorded on such a recording medium is optically or electromagnetically read, whereby the content of the specimens held on the microplate M can be grasped in the imaging apparatus 1. Particularly, in the case of attaching an optically readable recording medium to the lower surface of the microplate M, such information can be read by the camera 113.

In the imaging apparatus 1 configured as described above, when an instruction is received from the user, the control unit 15 controls the respective parts of the apparatus and performs a series of imaging processes including the imaging of the specimens by the camera 113. The content of an example of the imaging process is described below.

Figure 3:
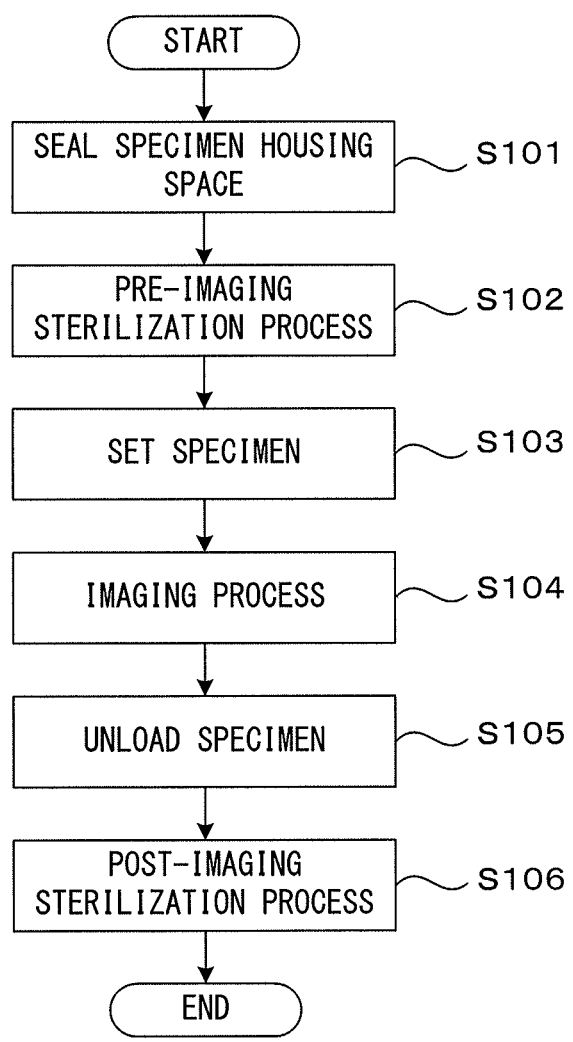
FIG. 3 is a flow chart which shows the flow of the imaging process in the first embodiment.

FIG. 3 is a flow chart which shows the flow of the imaging process in the first embodiment. First, before specimens are loaded, a pre-imaging sterilization process is performed. More specifically, the illumination unit 10 is placed on the top of the imaging unit 11 to seal the specimen housing space SP2 (Step S101). In this state, the sterilization light sources 103, 104, 115 and 116 are turned on to irradiate UV light in the specimen housing space SP2 for a predetermined time, whereby the interior of the specimen housing space SP2, particularly the holder 111 for holding the microplate M is sterilized (Step S102). By doing so, the specimens held on the microplate M to be subsequently loaded are prevented from being contaminated by contamination-causing substances remaining in the specimen housing space SP2. At this time, if the wall surfaces of the chambers 100, 110 are made of a material which reflects UV light well, light can reach even parts unreachable by direct light from the sterilization light source 103 and the like by being blocked by members in the specimen housing space SP2. The pre-imaging sterilization process is finished by turning off the sterilization light source 103 and the like.

Subsequently, the microplate M holding the specimens is set in the specimen housing space SP2 (Step S103). Specifically, the upper part of the specimen housing space SP2 is opened by retracting the illumination unit 10 to a retracted position located on an upper or lateral side, and the microplate M is loaded through an open part and placed on the holder 111. After the microplate M is placed on the holder 111, the illumination unit 10 is moved to a position right above the imaging unit 11 to seal the specimen housing space SP2. The movement of the illumination unit 10 and the loading of the microplate M may be manually performed by an operator or may be performed by appropriate moving mechanisms.

Note that the gas is desirably supplied into the specimen housing space SP2 from the gas discharge nozzle 118 in a state where the specimen housing space SP2 is open. By doing so, an airstream from the specimen housing space SP2 to the outside is generated, whereby the entrance of contamination-causing substances such as bacteria into the specimen housing space SP2 from the outside space can be suppressed. Further, also in a state where the specimen housing space SP2 is sealed, the entrance of contamination-causing substances from the outside space can be prevented by setting the air pressure in the specimen housing space SP2 to be slightly higher than in the outside space.

Subsequently, imaging by the camera 113 is performed (Step S104). Specifically, the illumination light source 101 of the illumination unit 10 is turned on, the camera 113 performs imaging while moving and scanning in the horizontal direction and, finally, an image of all the wells W of the microplate M is obtained.

When imaging is finished, the illumination unit 10 is retracted, whereby the specimen housing space SP2 is opened again and the specimens are unloaded together with the microplate M (Step S105). As a post-imaging sterilization process, UV light is irradiated from the sterilization light sources 103, 104, 115 and 116 for a predetermined time with the specimen housing space SP2 sealed as in the pre-imaging sterilization process (Step S106). By this, even if a part of the specimen is separated from the microplate M and remains and adheres to the holder 111 or in the specimen housing space SP2, the contamination of other specimens by this separated substance in the subsequent imaging is avoided. In this way, the series of imaging processes are completed.

As described above, in this embodiment, the sterilization light source 103 and the like for emitting light having a sterilization effect (specifically, UV light) are provided in the imaging apparatus 1, and the holder 111 on which the microplate M holding the specimens is to be placed and the specimen housing space SP2 housing this holder 111 are sterilized by UV light. By doing so, the contamination of specimens as imaging objects by contamination-causing substances such as fungi and bacteria remaining in the specimen housing space SP2, particularly those adhering to the holder 111 can be effectively avoided.

If the sterilization process is performed before specimens as imaging objects are loaded, it is prevented that contamination-causing substances remaining in the apparatus adhere to and contaminate the loaded specimens. Thus, an impact of contamination-causing substances during imaging can be avoided and the specimens can be unloaded after imaging while a clean state at the time of loading is maintained. Thus, changes in the specimens before and after imaging can be suppressed to a minimum level. Therefore, even if specimens stored in a culture booth are temporarily taken out for imaging and returned to the culture booth again after imaging, an impact of this takeout on the specimens is suppressed. This is particularly preferable in time lapse imaging in which specimens continuously cultured in a predetermined environment are imaged at regular time intervals a plurality of times.

By performing the sterilization process immediately before imaging, even if bacteria or the like proliferate by being left in a state adhering to the imaging apparatus 1, contamination caused by this can be reliably prevented.

On the other hand, if the sterilization process is performed immediately after specimens, whose imaging has been finished, are unloaded, parts of the specimens separated from the microplate M or contamination-causing substances such as bacteria having entered from outside when the specimens are loaded and unloaded can be avoided from remaining and proliferating in the apparatus by being sterilized.

Further, in this embodiment, a positive pressure relative to the surrounding space is applied to the specimen housing space SP2, whereby the entrance of contamination-causing substances coming from the outside space into the specimen housing space SP2 can be effectively prevented.

Second Embodiment

Next, a second embodiment of the imaging apparatus according to this invention is described. In this embodiment, a basic configuration of the apparatus main part is common to the first embodiment. In the following description, the same components as in the first embodiment are denoted by the same reference signs and not described in detail. Further, some components are neither shown nor described for the convenience of description. Unless otherwise particularly noted, it is assumed below that the respective components of the first embodiment described above are also provided in the second embodiment.

Figure 4:
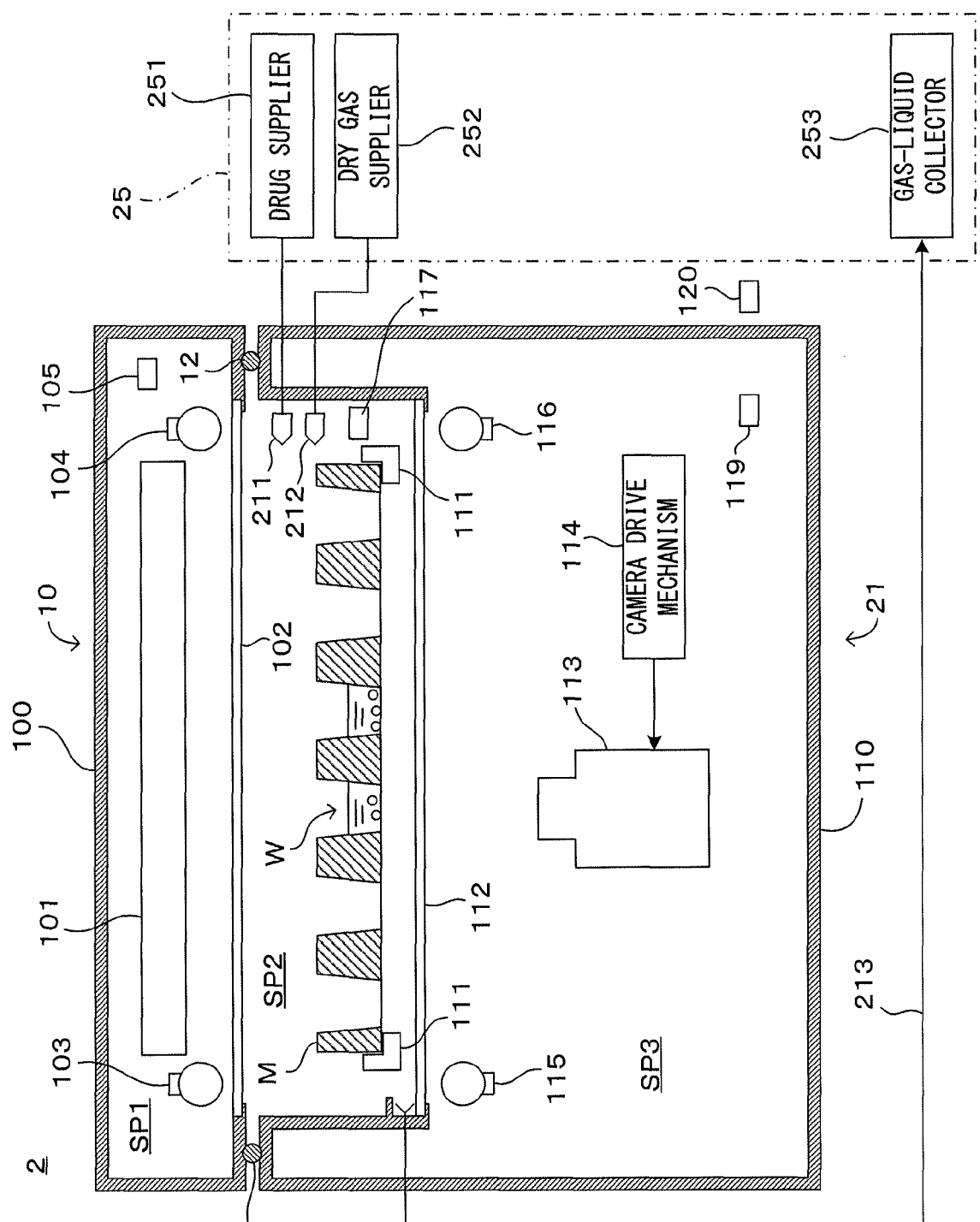
FIG. 4 is a diagram which shows a schematic configuration of an imaging apparatus according to the second embodiment of the invention.

FIG. 4 is a diagram which shows a schematic configuration of an imaging apparatus according to the second embodiment of the invention. More specifically, FIG. 4 is a block diagram showing a side sectional view of a main part of an imaging apparatus 2 of the second embodiment and the configuration of a control unit. The configuration of an illumination unit 10 is the same as in the first embodiment described above.

On the other hand, an imaging unit 21 of this embodiment additionally includes a drug discharge nozzle 211 for discharging a predetermined drug toward a specimen housing space SP2 and a dry gas discharge nozzle 212 for discharging dry gas toward the same space SP2. Note that the dry gas discharge nozzle 212 may double as a gas discharge nozzle 118 (FIG. 1). Further, a dry gas supplier 252 to be described later may double as a gas supplier 158.

A control unit 25 of this embodiment includes a drug supplier 251 for supplying the drug to the drug discharge nozzle 211 and the dry gas supplier 252 for supplying the dry gas to the dry gas discharge nozzle 212 in addition to each control block provided in the control unit 15 of the first embodiment.

The drug supplier 251 sends any one of liquids or gases illustrated below or a selective or appropriate mixture of these as a drug having a sterilization effect to the drug discharge nozzle 211 while maintaining a determined supply amount. The drug is discharged into the specimen housing space SP2 from the drug discharge nozzle 211, whereby the specimen housing space SP2 is sterilized. The drug supplier 251 may have a function of adjusting the temperature of the drug.

Alcohols, compounds containing chlorine as a sterilization component (e.g. sodium hypochlorite), or solutions containing them can be, for example, used as liquid drugs. Besides these, liquids showing a sterilization effect on various bacteria or specific bacteria can also be used as drugs. Particularly, if the type of bacteria contained in specimens or having a possibility of being mixed into is known, a drug effective to such bacteria or the like can be appropriately selected and used.

Vaporized alcohols, compounds containing chlorine as a sterilizing component (chlorine gas), ethylene oxide, ozone gas and the like can be used as gaseous drugs. Out of these, ozone gas may be supplied from the drug supplier 251 or may be generated in the specimen housing space SP2 by turning on a sterilization light source 103 and the like.

Note that respective members as partition walls surrounding the specimen housing space SP2, i.e. chambers 100, 110, transparent windows 102, 112 and a packing 12, various nozzles and sensors are desirably made of materials corrosive resistant to the drug to be used. For example, quartz glass can be used for the transparent windows 102, 112. Further, silicon resin or fluororesin can be, for example, used for the packing 12. Further, a stainless steel material can be, for example, used for members which require no light permeability and fluororesin coating may be applied to further enhance corrosion resistance to drugs and ozone.

The control unit 25 includes a gas-liquid collector 253, which communicates with the specimen housing space SP2 via a discharge path 213. The drug or gas supplied to the specimen housing space SP2 are collected into the gas-liquid collector 253 via the discharge path 213. A suction unit such as a suction pump may be appropriately provided on the discharge path 213. In this case, to improve collection efficiency, collection may be performed with pressure differences between air pressures in the respective spaces SP2, SP3 and an atmospheric pressure maintained. The gas-liquid collector 253 includes a liquid-gas separator and separates the collected fluid into liquid components and gas components and individually collects them. Since a drain structure for discharging the gas and the like from the chambers and the gas-liquid separator are known, they are not described in detail here.

In the imaging apparatus 2 configured as described above, an imaging process is performed in accordance with the flow chart shown in FIG. 3 as in the first embodiment. However, the content of the sterilization process (pre-imaging sterilization process in Step S102 and post-imaging sterilization process in Step S105) differs from that in the first embodiment.

Figure 5:
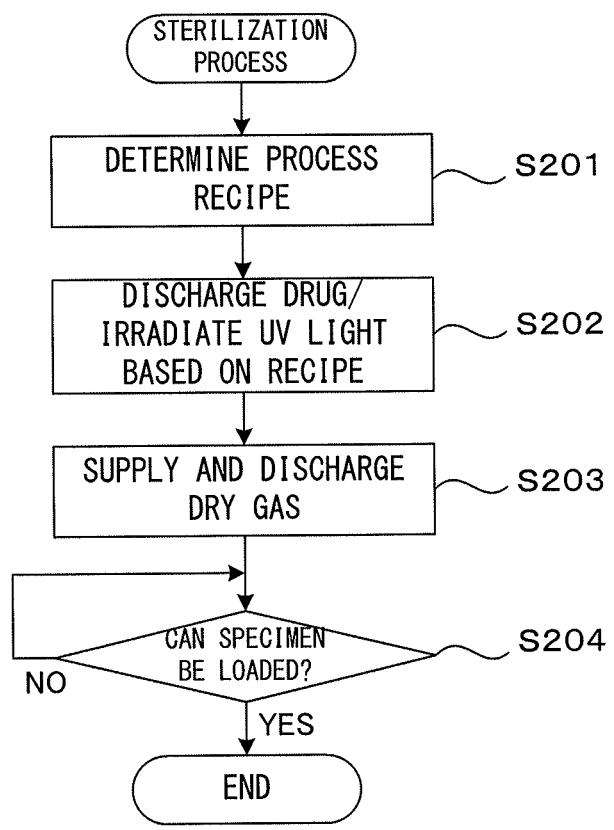
FIG. 5 is a flow chart which shows a sterilization process in the second embodiment.

FIG. 5 is a flow chart which shows a sterilization process in the second embodiment. Firstly, the control unit 25 selects one sterilization process recipe corresponding to a situation out of a plurality of sterilization process recipes prepared in advance and determines it as a process recipe to be executed (Step S201). Process conditions composed of a combination of process parameters such as the selection of a drug to be used, the use of UV light, the density and temperature of the drug, a process time differ from each other among the plurality of process recipes, and any one of the process recipes is selected according to the type of specimens and purpose of the process.

In the pre-imaging sterilization process (Step S102 of FIG. 3) before specimens to be imaged are loaded, an impact of residues in the previous imaging can be reliably eliminated and the contamination of later specimens can be prevented, for example, by selecting the process recipe corresponding to the type of specimens used in the imaging process immediately before this imaging process. Further, if the process recipe corresponding to the type of specimens used in the next imaging process is selected, the process conditions having less impact on the specimens can be applied. On the other hand, in the post-imaging sterilization process (Step S105 of FIG. 3) after imaging is finished, the process recipe necessary to prevent the proliferation of the specimens used in imaging and the contamination of next specimens thereby is selected.

For these purposes, information of a recording medium attached in an attachment area M4 of a microplate M can be used. Further, a list of selectable process recipes may be displayed on a display 17 and a user may be let to select any one according to the purpose. The selection input of the recipe can be received by an input receiver 16. Further, the process conditions may be designated by the user.

When the process recipe is determined, the specimen housing space SP2 is sterilized in accordance with the determined process recipe (Step S202). Specifically, if the supply of a drug is determined in the process recipe, the designated drug is sent from the drug supplier 251 to the drug discharge nozzle 211 and discharged into the specimen housing space SP2 from the drug discharge nozzle 211. Instead of or in addition to this, if the irradiation of UV light is determined in the process recipe, UV light is irradiated to the specimen housing space SP2 by turning on the sterilization light source 103 and the like. Further, a sterilization effect may be further improved by using both the drug and UV light.

After the supply of the drug and/or the irradiation of UV light are continued for a predetermined time, this is stopped. Subsequently, predetermined dry gas, e.g. dry air or inert gas such as nitrogen gas is supplied toward the dry gas discharge nozzle 212 from the dry gas supplier 252 and discharged into the specimen housing space SP2 from the dry gas discharge nozzle 212 (Step S203). In this way, the drug remaining in the specimen housing space SP2 is discharged via the discharge path 213 and collected into the gas-liquid collector 253. Particularly, if the drug used for sterilization is liquid, the drying of the drug can be more accelerated if heated gas is supplied to the specimen housing space SP2.

If sterilizing components remaining in the specimen housing space SP2 are reduced to a necessary and sufficient level and the specimen housing space SP2 returns to a temperature/humidity environment suitable for the existence of cells or the like, new specimens can be received. If this state is reached (Step S204), the sterilization process is finished and a return is made to the process of FIG. 3.

As described above, the imaging apparatus 2 of this embodiment has a configuration for realizing a function of supplying the drug having the sterilization effect to the specimen housing space SP2 and a function of preparing a plurality of process recipes having different process conditions and selectively executing them in addition to the configuration of the imaging apparatus 1 of the first embodiment. This enables sterilization by the drug in this embodiment in addition to functions and effects of the imaging apparatus 1 of the first embodiment and an effective sterilization process can be performed also on contamination-causing substances for which it is difficult to achieve a sufficient sterilization effect only by UV irradiation.

Further, by selectively executing the plurality of process recipes having process conditions different from each other, the sterilization process recipe corresponding to the type of specimens used before the sterilization process or specimens to be used after the sterilization process can be applied and the effect of the sterilization process can be made more reliable. Further, by performing the next process after a state where cells or the like can exist is reached after sterilization is performed, an impact of the remaining drug or the like on specimens to be loaded into the specimen housing space SP2 anew can be prevented.

Third Embodiment

Next, a third embodiment of the imaging apparatus according to this invention is described. The imaging apparatus of the third embodiment described below is designed to realize an additional function in addition to the functions of the imaging apparatuses of the first and second embodiments described above by adding a new configuration to the imaging apparatus of the first or second embodiment. Here is described a case based on the imaging apparatus 1 of the first embodiment and the configuration newly added in the third embodiment is mainly described. Note that the same components as in the first embodiment are denoted by the same reference signs and not described in detail. Further, some components common to the apparatus of the first embodiment are neither shown nor described for the convenience of description. Unless otherwise particularly noted, it is assumed below that the respective components of the first embodiment described above are also provided in the third embodiment.

Further, although new effects and functions are achieved by adding the new configuration to the apparatus of the first embodiment in this third embodiment, the new effects and functions described below are achieved also in an embodiment in which this new configuration is added to the apparatus of the second embodiment.

Figure 6:
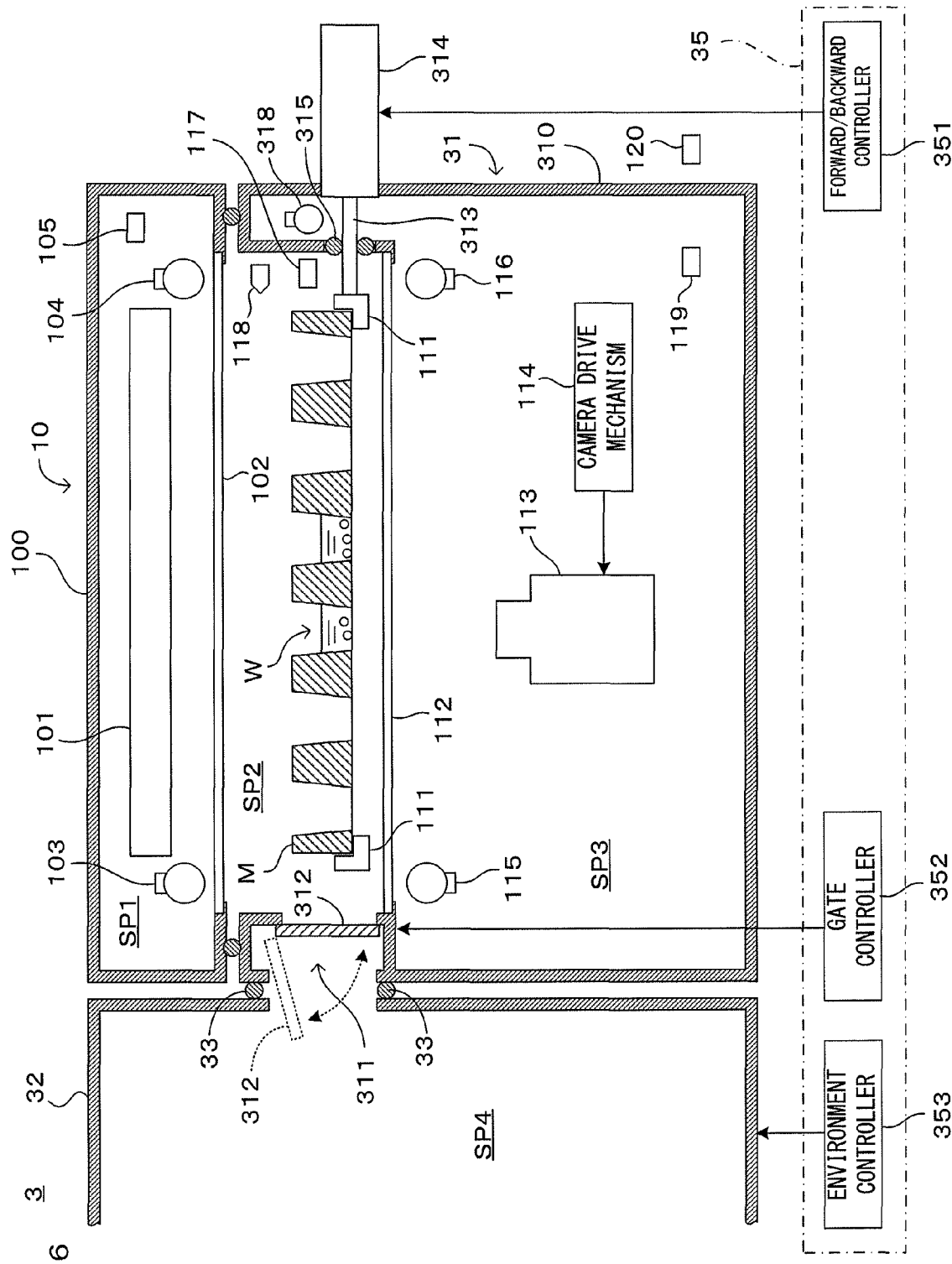
FIG. 6 is a diagram which shows a schematic configuration of an imaging apparatus according to the third embodiment of the invention.

FIG. 6 is a diagram which shows a schematic configuration of an imaging apparatus according to the third embodiment of the invention. More specifically, FIG. 6 is a block diagram showing a side sectional view of a main part of an imaging apparatus 3 of the third embodiment and the configuration of a control unit. In this embodiment, the configuration of an illumination unit 10 is the same as in the first embodiment described above.

On the other hand, in an imaging unit 31 of this embodiment, the shape of a chamber 310 differs from that (chamber 110) of the first embodiment. Specifically, an opening 311 is provided on a lateral part of the chamber 310 and lateral to a specimen housing space SP2. The opening 311 approximately has such an opening size that a microplate M can be passed therethrough while being kept in a horizontal posture, and an openable and closable gate member 312 is attached to this opening 311. In a state where the gate member 312 is closed with respect to the opening 311, the opening 311 is closed by the gate member 312 and the specimen housing space SP2 is sealed. On the other hand, in a state where the gate member 312 is opened, the microplate M can be loaded into and unloaded from the specimen housing space SP2 through the opening 311. The gate member 312 is controlled to be opened and closed by a gate controller 352 provided in a control unit 35.

An incubator unit 32, an internal space SP4 of which is kept in a constant temperature/humidity environment, is provided at a side of the opening 311 opposite to the specimen housing space SP2. Since a known incubator system can be applied as the configuration of the incubator unit 32, the configuration of the incubator unit 32 is not described in detail here. For example, by applying a known glove box incubator system, specimens can be operated in the incubator unit 32 without being exposed to outside space.

The incubator unit 32 is mounted to close the opening 311 of the chamber 310 via a packing 33, and the internal space SP4 thereof links to the specimen housing space SP2 via the opening 311. More specifically, in a closed state of the gate member 312, the specimen housing space SP2 and the internal space SP4 of the incubator unit 32 are separated by the gate member 312. On the other hand, in an open state of the gate member 312, the specimen housing space SP2 and the internal space SP4 of the incubator unit 32 communicate through the opening 311.

Further, in the imaging unit 31, a support rod 313 is attached to a holder 111 for holding the microplate M in the specimen housing space SP2 and also to a forward/backward drive mechanism 314. The forward/backward drive mechanism 314 moves the support rod 313 forward and backward (lateral direction of FIG. 6) in response to a control command from a forward/backward controller 351 provided in the control unit 35. In this way, the holder 111 is movable in a horizontal direction. These forward and backward movements are linked with the opening and closing of the gate member 312 and the holder 111 can convey the microplate M between the specimen housing space SP2 and the incubator unit 32 through the opening 311 by moving forward and backward while holding the microplate M.

The support rod 313 is provided to penetrate through a side wall of the specimen housing space SP2 and a packing 315 for holding airtightness is provided between this side wall and the support rod 313. Further, a sterilization light source 318 for sterilizing a part of the support rod 313, which moves into and out of the specimen housing space SP2, is provided in an internal space SP3 of the chamber 311. In this way, the contamination of specimens from the support rod 313 via the holder 111 is prevented.

The control unit 35 of this embodiment includes an environment controller 353 for controlling temperature/humidity and atmospheric gas density ($O_2$, $CO_2$, $N_2$, etc.) environments of the internal space SP4 of the incubator unit 32 and the respective components of the control unit 15 of the first embodiment described above in addition to the above.

In such a configuration, the specimens can be imaged by moving the microplate M to the specimen housing space SP2 of the imaging unit 31 according to needs while culturing or storing the specimens in the microplate M placed still in the internal space SP4 of the incubator unit 32. The microplate M holding the specimens can be returned to the incubator unit 32 after imaging is finished. Since the specimens are not exposed to outside atmosphere during this time, the contamination of the specimens due to imaging is effectively prevented. The imaging apparatus 3 may be used to image other specimens, therefore the imaging process in this apparatus is configured as follows to make assurance doubly sure on the contamination prevention of specimens.

FIG. 7 is a flow chart which shows the flow of the imaging process in the third embodiment. In a stage before the imaging process is performed, the microplate M is stored in the incubator unit 32 and the gate member 312 is closed. In this state, the pre-imaging sterilization process is performed (Step S301).

Subsequently, the gate member 312 is opened and the microplate M is loaded into the specimen housing space SP2 from the internal space SP4 of the incubator unit 32 through the opening 311 (Step S302). After loading, the gate member 312 is closed and the specimens are imaged as in the first embodiment (Step S303).

After imaging is finished, the gate member 312 is opened again and the microplate M is unloaded to the incubator unit 32 (Step S304). After the gate member 312 is closed, the post-imaging sterilization process is performed (Step S305). If the above process is regularly repeated, it is possible to perform time lapse imaging in which one specimen is imaged at different timings a plurality of times.

As described above, this embodiment is so configured that the incubator unit 32 is built in the imaging apparatus 3, the internal space SP4 of the incubator unit 32 and the specimen housing space SP2 of the imaging unit 32 are connected and the specimens are conveyed between the two spaces. According to such a configuration, the specimens can be conveyed between the incubator unit 32 for storing the specimens and the imaging unit 31 for imaging the specimens without being exposed to outside space, and the contamination of the specimens can be more effectively prevented.

Fourth Embodiment

Figure 8:
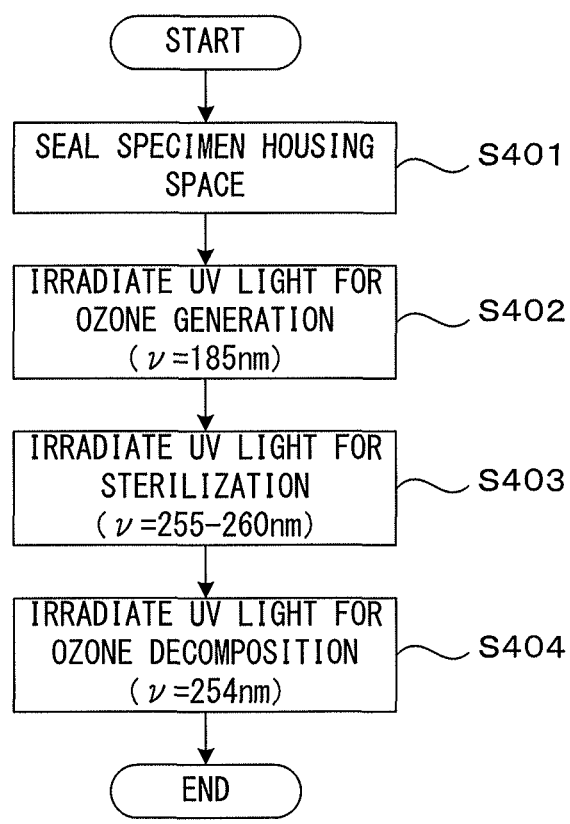
FIG. 8 is a flow chart which shows the operation of an imaging apparatus according to a fourth embodiment of the invention.

FIG. 8 is a flow chart which shows the operation of an imaging apparatus according to a fourth embodiment of the invention. The configuration of the imaging apparatus of the fourth embodiment described below is basically identical to that of the first embodiment (FIG. 1) described above and the operation thereof is partly different. It is assumed that the wavelength of UV light to be emitted is switchable for a sterilization light source 103 and the like. A process shown in FIG. 8 is a sterilization process performed in the fourth embodiment instead of the pre-imaging sterilization process and the post-imaging sterilization process performed in the first embodiment. Both the pre-imaging sterilization process and the post-imaging sterilization process may be replaced by the process of FIG. 8 or only either one of them may be replaced.

In the sterilization process of this embodiment, a substance having a sterilization effect is generated in a specimen housing space SP2 instead of supplying gas or liquid as a drug having a sterilization effect. For example, ozone gas having a sterilization effect can be supplied in the specimen housing space SP2 by converting oxygen present in the specimen housing space SP2 into ozone. Specifically, after the specimen housing space SP2 is sealed (Step S401) as in the first embodiment, light having a center wavelength of 185 nm is first irradiated as UV light for ozone generation to the specimen housing space SP2 from the sterilization light source 103 or the like (Step S402). UV light (ultraviolet light) is known to have a wavelength for ozone generation and a wavelength for ozone decomposition respectively. Here, UV light having a wavelength for ozone generation is irradiated. In this way, oxygen in the specimen housing space SP2 is converted into ozone and ozone is generated in the specimen housing space SP2.

Subsequently, the wavelength of the UV light from the sterilization light source 103 or the like is changed to 255 nm to 260 nm to have a higher sterilization effect (Step S402). In this way, a sterilization effect by the UV light is exhibited in addition to the sterilization effect by ozone in the specimen housing space SP2, whereby a higher sterilization effect can be obtained. After this state is maintained for a predetermined time, the wavelength of the UV light from the sterilization light source 103 or the like is changed to 254 nm for ozone decomposition (Step S404). This wavelength has an effect to decompose ozone and ozone in the specimen housing space SP2 is decomposed to be detoxified, whereby an impact on specimens to be loaded can be prevented. Note that the UV light for sterilization and that for ozone decomposition may have the same wavelength.

As described above, in this embodiment, the UV light for ozone generation, that for sterilization and that for ozone decomposition are successively irradiated into the specimen housing space SP2. This enables the interior of the specimen housing space SP2 to be more reliably sterilized by a sterilization effect by the UV light and ozone. Along with this, it can be prevented that ozone toxic to the specimen in the specimen housing space SP2 after the sterilization process remains.

Fifth Embodiment

Figure 9:
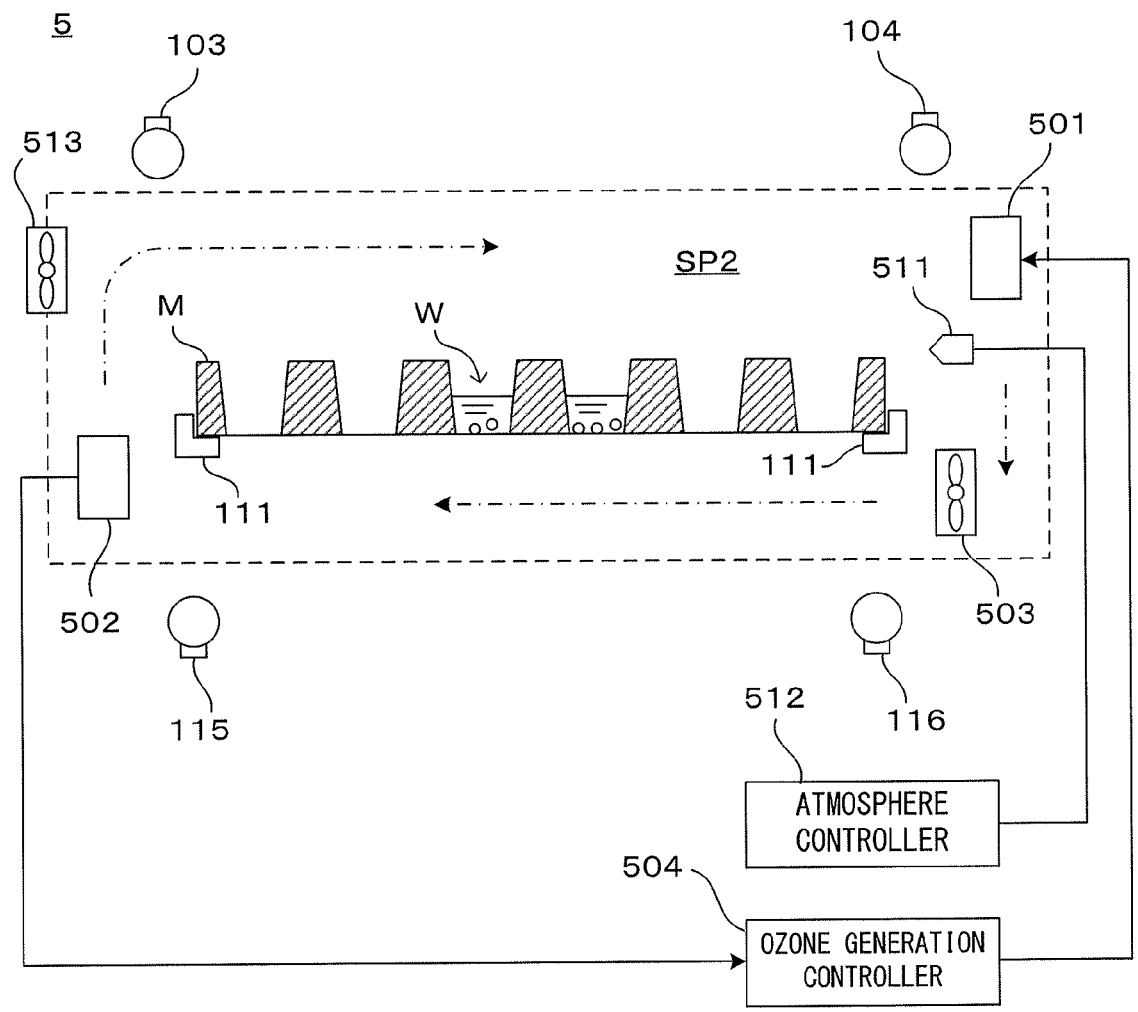
FIG. 9 is a diagram which shows a main configuration of an imaging apparatus according to a fifth embodiment of the invention.

FIG. 9 is a diagram which shows a main configuration of an imaging apparatus according to a fifth embodiment of the invention. Note that, components common to the first embodiment are denoted by the same reference signs or not described in FIG. 9 and the following description. Unless otherwise particularly noted, it is assumed below that the respective components of the first embodiment described above are also provided in the fifth embodiment.

Also in this embodiment, a substance having a sterilization effect is generated in a specimen housing space SP2 as in the fourth embodiment. Specifically, an ozone generator 501 such as a discharge type ozone generator capable of generating ozone as a sterilization component from oxygen in the specimen housing space SP2, an ozone concentration meter 502 for measuring an ozone concentration and a circulation fan 503 for circulating the air in the specimen housing space SP2 are provided in this space SP2. Since ozone has a higher specific gravity than air, the ozone generator 501 is provided in an upper part of the specimen housing space SP2 and the ozone concentration meter 502 is provided in a lower part of the specimen housing space SP2. Arrows shown in dashed-dotted line in FIG. 9 diagrammatically indicate an airstream formed in the specimen housing space SP2 by the circulation fan 503.

Further provided are a gas supply nozzle 511 for supplying various gases into the specimen housing space SP2 and an exhaust fan 513 for discharging gases in the specimen housing space SP2 to outside. It is preferable to provide a check valve, a sealing shutter or the like as a reverse flow preventing means for preventing the inflow of outside air when the exhaust fan 513 is not used.

The ozone generator 501 is controlled by an ozone generation controller 504, which controls the ozone generator 501 based on an output from the ozone concentration meter 502 to generate ozone of a predetermined concentration in the specimen housing space SP2. Further, the gas supply nozzle 511 is connected to an atmosphere controller 512 and supplies various gases supplied from the atmosphere controller 512 according to a process recipe into the specimen housing space SP2. For example, oxygen can be supplied into the specimen housing space SP2 to increase an ozone generation amount in the specimen housing space SP2.

According to such a configuration, ozone gas efficiently generated by the ozone generator 501 is spread in the specimen housing space SP2 by the operation of the circulation fan 503 and the interior of the specimen housing space SP2 can be powerfully sterilized by ozone in a short time. Of course, it can be used together with UV light irradiation from a sterilization light source 103 or the like. By properly controlling an ozone concentration by the ozone concentration meter 502 and the ozone generation controller 504, it is possible to prevent excessive ozone generation, shorten a time required for sterilization and prevent an impact on a surrounding environment.

To efficiently generate ozone in the specimen housing space SP2, oxygen gas may be introduced into the specimen housing space SP2 from the gas supply nozzle 511 prior to or simultaneously with the operation of the ozone generator 501. Further, by operating the exhaust fan 513 to exhaust the gas while introducing clean air from the gas supply nozzle 511 after the sterilization process is finished, ozone remaining in the specimen housing space SP2 can be discharged in a short time and an environment suitable for the subsequent imaging process can be set. At this time, by observing the ozone concentration in the specimen housing space SP2 by the ozone concentration meter 502, ozone can be more reliably discharged. A specific operation of the sterilization process can be, for example, set as follows.

Figure 10:
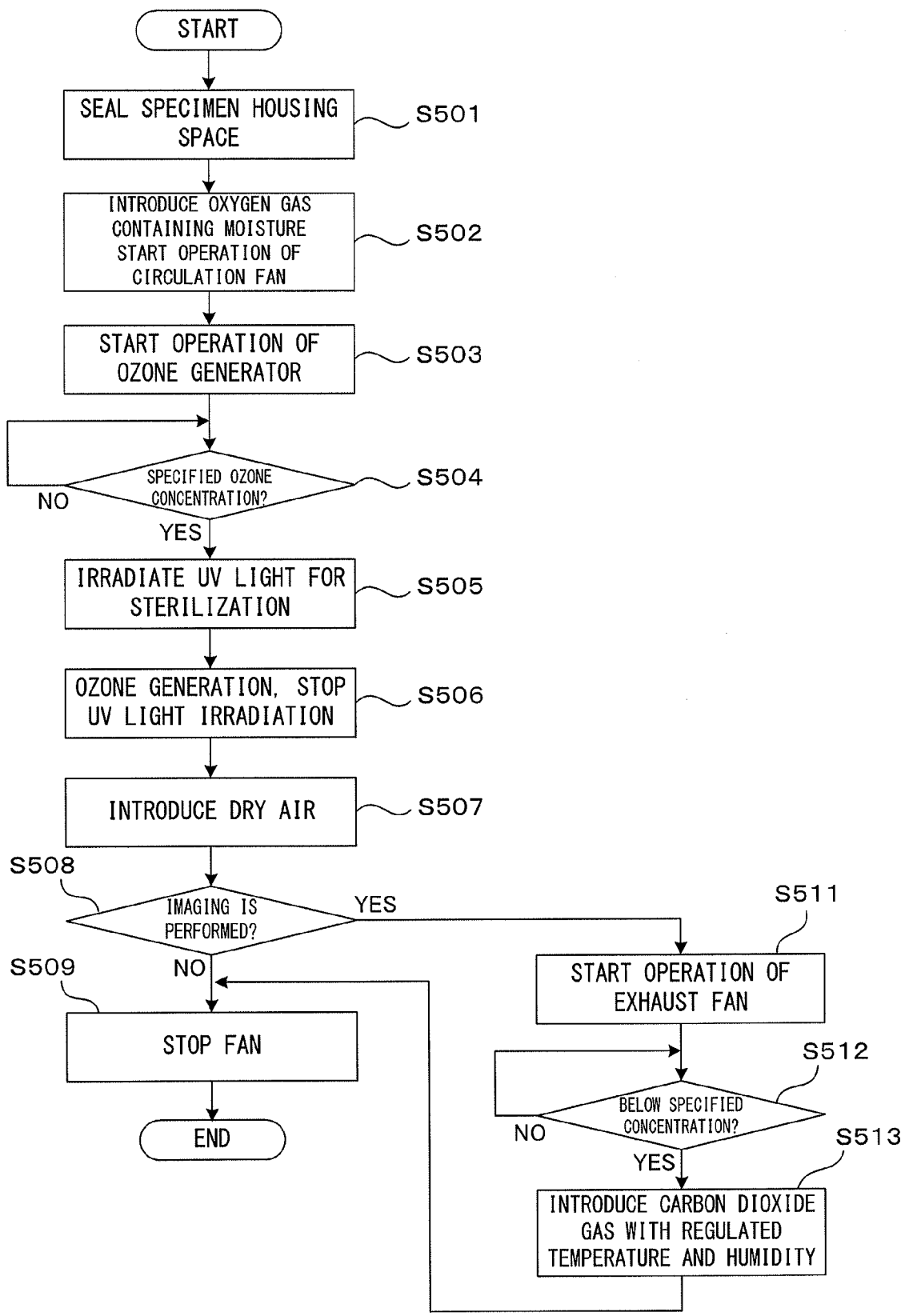
FIG. 10 is a flow chart which shows a sterilization process in the fifth embodiment.

FIG. 10 is a flow chart which shows a sterilization process in the fifth embodiment. In this process, after the specimen housing space SP2, into which a specimen is not loaded yet, is sealed (Step S501) as in the first embodiment, oxygen containing moisture is introduced into the specimen housing space SP2 from the gas supply nozzle 511 and the operation of the circulation fan 503 is started (Step S502). Subsequently, the operation of the ozone generator 501 is started (Step S503) to set an ozone atmosphere in the specimen housing space SP2. Oxygen gas containing moisture is introduced to supply oxygen as an ozone source and obtain a further sterilization effect by ionizing water molecules.

When the ozone concentration measured by the ozone concentration meter 502 reaches a specified concentration at which a sufficient sterilization effect is achieved (Step S504), the irradiation of UV light for sterilization is started from the sterilization light source 103 or the like (Step S505). By keeping this state for a predetermined time, the specimen housing space SP2 is sterilized by a sterilization effect by ozone and that by UV light. After the elapse of the predetermined time, ozone generation by the ozone generator 501 and UV light irradiation from the sterilization light source 103 or the like are stopped (Step S506). Subsequently, dry air is introduced from the gas supply nozzle 511 to dry the specimen housing space SP2 and dilute ozone (Step S507). Note that the introduction of dry air is not essential. For example, the ozone atmosphere may be left in the specimen housing space SP2 when the next imaging process is not subsequently performed after the sterilization process.

The subsequent operation differs depending on whether the imaging process is to be subsequently performed (Step S508). Unless the imaging process is performed, the circulation fan 503 is stopped and the process is finished (Step S509). On the other hand, if the imaging process is subsequently performed, the exhaust fan 513 is operated (Step S511) following the introduction of dry air and the ozone atmosphere in the specimen housing space SP2 is replaced by dry air.

If the ozone concentration is reduced to or below the specified concentration at which the specimen is not affected (Step S512), carbon dioxide gas ($CO_2$) with regulated temperature and humidity is introduced into the specimen housing space SP2 from the gas supply nozzle 511 (Step S513). Gas temperature is preferably about the same as temperature in an incubator for culturing specimens and, for example, set at about 37° C. suitable for culturing cells. Further, to prevent cells from being killed in a dry atmosphere, the gas has a suitable humidity. Since imaging at a high resolution particularly takes time, the atmosphere including temperature and humidity in the specimen housing space SP2 is desirably set close to culturing conditions in the incubator. For this purpose, a means for detecting temperature or humidity may be provided in the specimen housing space SP2.

After the atmosphere in the specimen housing space SP2 is set at conditions suitable for imaging, the circulation fan 503 and the exhaust fan 513 are stopped (Step S509), the sterilization process is finished and a state is set where a specimen for imaging can be loaded.

As described above, in this embodiment, the interior of the specimen housing space SP2 can be powerfully sterilized by ozone in a short time by installing the discharge type ozone generator 501 and the circulation fan 503 in the specimen housing space SP2. Further, the imaging process can be performed without affecting the specimen by exhausting ozone gas after the sterilization process in a short time and setting an environment suitable of the existence of cells or the like. Note that although the circulation fan 503 is provided to circulate ozone in the specimen housing space SP2 in this embodiment, an agitating means for agitating gas in the specimen housing space SP2 is not limited to this. For example, an airstream may be generated in the specimen housing space SP2 by causing gas to flow in from outside.

Sixth Embodiment

Figure 11:
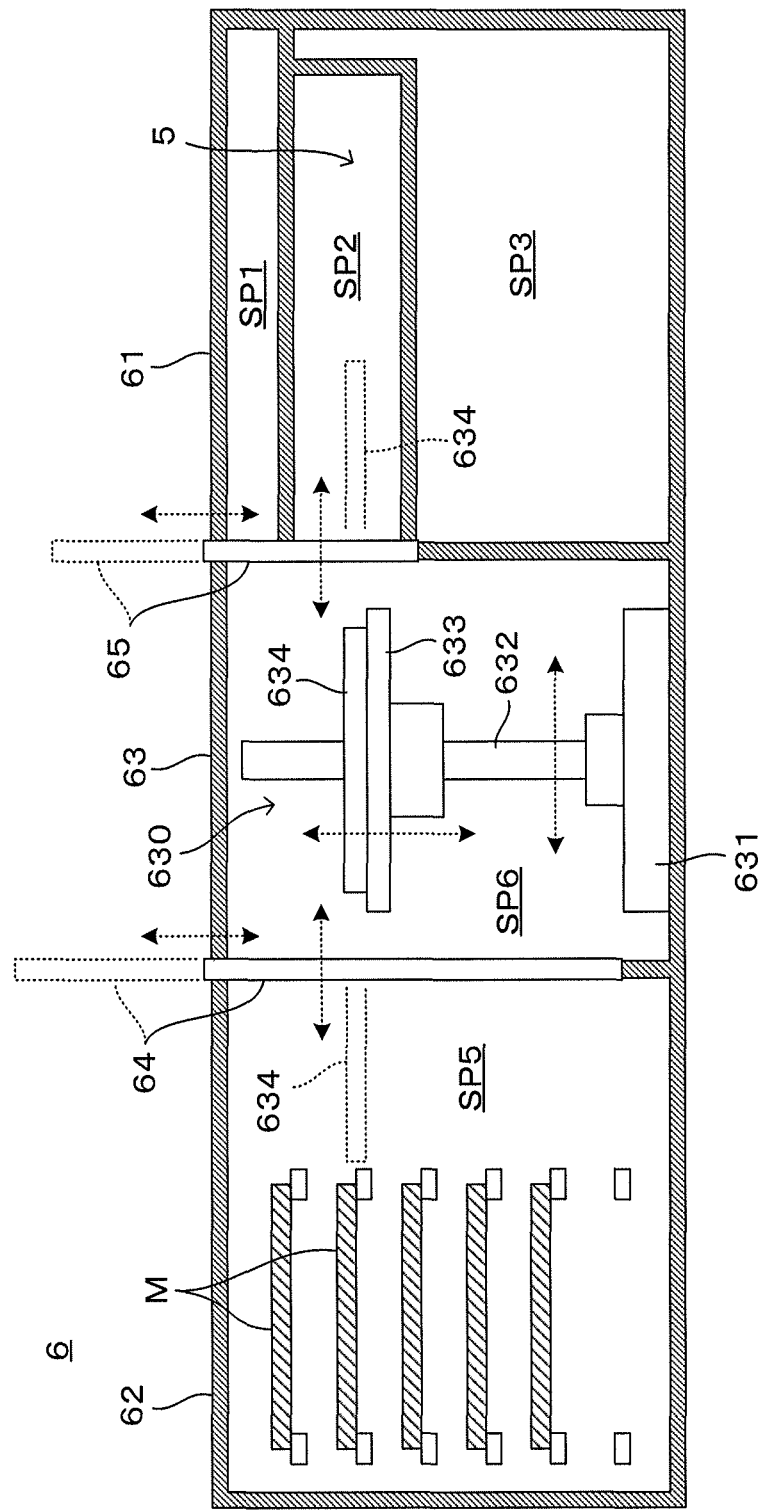
FIG. 11 is a diagram which shows a schematic configuration of an imaging apparatus according to a sixth embodiment of the invention.

FIG. 11 is a diagram which shows a schematic configuration of an imaging apparatus according to a sixth embodiment of the invention. More specifically, FIG. 11 is a side view showing an example of an observation system provided with an imaging apparatus according to this invention. This observation system 6 is structured such that an imaging unit 61 and a plate stocker 62 are connected via a specimen transfer chamber 63. An imaging apparatus having the same structure as the imaging apparatus 5 of the fifth embodiment can be, for example, used as the imaging unit 61. The configuration thereof is as described above and only the entire configuration of the system is shown in FIG. 11 with the configuration of the imaging unit 61 omitted.

The plate stocker 62 is a storage means for temporarily storing one or more microplates M to be subjected to an imaging process in an atmosphere-controlled sealed space. As in the internal space SP4 of the incubator unit 32 of the third embodiment, an internal space SP5 of the plate stocker 62 is maintained in an atmosphere and a temperature/humidity environment suitable for culturing cells and also has a function as an incubator. Further, a plurality of microplates M may be stored in a state separated from each other.

A transfer unit 630 for transferring the microplates M between the plate stocker 62 and the imaging unit 61 are disposed in the internal space SP6 of the specimen transfer chamber 63. The transfer unit 630 includes a column member 632 standing movably in a horizontal direction relative to a base 631 fixed in the specimen transfer chamber 63, and a slide stage 633 is attached to this column member 632 movably in a vertical direction. A specimen holding stage 634 is provided on the slide stage 633, and the specimen holding stage 634 is movable in the horizontal direction relative to the slide stage 633.

An opening is formed in a partition wall between the plate stocker 62 and the specimen transfer chamber 63, and a shutter member 64 capable of opening and closing the opening is provided to cover the opening. In a state where the shutter member 64 is moved upward as shown in dotted line in FIG. 11, the internal space SP5 of the plate stocker 62 and an internal space SP6 of the specimen transfer chamber 63 communicate. The specimen holding stage 634 moves into the internal space SP5 of the plate stocker 62 from the specimen transfer chamber 63 through the opening between the both and unloads one of the microplates M stored in the plate stocker 62. Further, the specimen holding stage 634 loads the microplate M placed on the specimen holding stage 634 into the plate stocker 62.

On the other hand, an opening is also formed in a partition wall between the imaging unit 61 and the specimen transfer chamber 63 and a shutter member 65 capable of opening and closing the opening is provided to cover the opening. In a state where the shutter member 65 is moved upward, a specimen housing space SP2 of the imaging unit 61 and the internal space SP6 of the specimen transfer chamber 63 communicate. The specimen holding stage 634 moves into the specimen housing space SP2 of the imaging unit 61 through the opening between the both, thereby loading the microplate M into the specimen housing space SP2 and unloading the microplate M from this space SP2.

In the observation system 6 thus configured, one or more microplates M stored in the plate stocker 62 can be successively transferred to the imaging unit 61 to be imaged and can be returned to the plate stocker 62 after imaging. During this time, the microplates M are not exposed to outside air.

Here, to prevent the contamination of specimens, the internal space SP6 of the specimen transfer chamber 63 also needs to be sterilized. A sterilization means may be installed in the specimen transfer chamber 63 for that purpose, but the following configuration is adopted in this embodiment. Specifically, the sterilization process (FIG. 10) of the fifth embodiment described above is performed in a state where the shutter member 64 partitioning the plate stocker 62 and the specimen transfer chamber 63 is closed and, on the other hand, the shutter member 65 provided between the imaging unit 61 and the specimen transfer chamber 63 is opened.

The internal space SP6 of the specimen transfer chamber 63 communicates with the specimen housing space SP2 of the imaging unit 61 and is sterilized together with the specimen housing space SP2. More specifically, ozone gas generated by the ozone generator 501 provided in the specimen housing space SP2 is blown by the circulation fan 503, and the internal space SP6 of the specimen transfer chamber 63 is also filled with ozone gas for sterilization. At this time, by closing the shutter member 64, an impact on the specimens held on the microplates M in the plate stocker 62 is avoided. For this purpose, the partition wall between the plate stocker 62 and the specimen transfer chamber 63 and the shutter member 64 is desirably made of a material which does not have a property of allowing the transmission of ultraviolet light.

Note that, in the system assuming that the internal space SP6 of the specimen transfer chamber 63 and the specimen housing space SP2 are sterilized together, a means provided in the specimen housing space SP2 for sterilization, e.g. the ozone generator may be installed in the internal space SP6 of the specimen transfer chamber 63.

As described above, in this embodiment, a plurality of microplates M can be successively imaged without being exposed to outside air by providing the specimen transfer chamber 63 including the transfer unit 630 between the plate stocker 62 for storing the microplates M and the imaging unit 61. The shutter member 64 is provided between the plate stocker 62 and the specimen transfer chamber 63 and the shutter member 65 is provided between the imaging unit 61 and the specimen transfer chamber 63. In this way, the internal space SP6 of the specimen transfer chamber 63 and the specimen housing space SP2 of the imaging unit 61 can be sterilized together without affecting the specimens stored in the plate stocker 62.

<Miscellaneous>

As described above, in the above respective embodiments, the microplate M corresponds to a "specimen container" of the invention and the holder 111 holding this functions as a "holder" of the invention. Further, in the above respective embodiments, the camera 113 functions as an "imager" of the invention. Further, the control units 15, and 35 of the first, second and third embodiments respectively function as a "controller" of the invention. Further, the chambers 100 and 110 which form the specimen housing space SP2 by being united with each other function together as a "chamber" of the invention.

Further, the sterilization light sources 103, 104, 115, 116 and 318 in the respective embodiments respectively function as a "sterilizer" of the invention and, simultaneously, function as an "electromagnetic wave irradiator" of the invention. Further, in the second and third embodiments, the drug supplier 251 and the drug discharge nozzle 211 function as the "sterilizer" of the invention. Further, the pressure sensors 105, 117, 119 and 120, the gas supplier 158 and the gas discharge nozzle 118 function together as a "positive pressure application unit" of the invention.

Further, in the second embodiment, the discharge path 213 and the gas-liquid collector 253 function as a "discharger" of the invention. Further, in the third embodiment, the incubator unit 32 functions as a "specimen storage" of the invention, whereas the gate member 312 functions as a "gate member" of the invention. Furthermore, the support rod 313, the forward/backward drive mechanism 314 and the forward/backward controller 351 function together as a "conveyor" of the invention.

Note that the invention is not limited to the above embodiments and various changes other than those described above can be made without departing from the gist of the invention. For example, although the sterilization light source 103 and the like are provided as the sterilizer in any of the above respective embodiments, sterilization may be performed, for example, only by a drug without providing the sterilization light sources. Further, electromagnetic waves irradiated to the holder for the purpose of sterilization are not limited to UV light and any arbitrary electromagnetic waves having a sterilization effect can be used. For example, microwaves may be used.

Further, although ozone remaining in the specimen housing space SP2 is reduced by the irradiation of UV light for ozone decomposition in the fourth embodiment or by providing the exhaust fan 513 in the fifth embodiment, a catalyst having a function of decomposing ozone may be installed in the specimen housing space SP2. For example, since a manganese dioxide based catalyst becomes most active and has a high ozone decomposition effect around 40° C., it is suitable as a catalyst which acts on a culture temperature condition of specimens.

Further, the above respective embodiments are so configured that the sterilization process is performed before and after imaging. However, as described above, the pre-imaging sterilization process and the post-image sterilization process respectively have independent effects and it is not always necessary that these processes are paired. That is, the sterilization process may be performed only either before or after imaging.

Further, in the above respective embodiments, the space enclosed by the lower surface of the illumination unit 10 and the upper surfaces of the imaging unit 11 and the like serves as the specimen housing space SP2. However, a configuration for forming a space for storing specimens (microplate M) is not limited to this. For example, specimens may be stored in a chamber having a hollow interior and transparent upper and lower surfaces and the specimens may be illuminated from above the chamber and imaged below the chamber. Further, illuminating and imaging directions are also not limited to those of the above embodiments and the illumination light source and the camera may be respectively arranged either above or below the specimens. Further, although air pressures in the respective spaces inside and outside the apparatus are adjusted by providing the pressure sensors in the respective spaces in the above embodiments, it is sufficient to keep a pressure balance in the respective spaces at the one described above and there is no limitation to the above configuration. For example, the pressure sensors can be omitted, for example, by providing a simple positive pressure application unit in the specimen housing space SP2 and maintaining the air pressure in the specimen housing space SP2 higher than in the other spaces.

Further, the specimen container of the invention is not limited to the microplate as in the above embodiments and an arbitrary one can be used. For example, the invention can also be applied to an apparatus for imaging a specimen cultured in a test tube from a lateral side.

Further, for example, a chamber may be provided which forms a specimen housing space capable of storing the specimen container, the holder may be provided in the specimen housing space and the sterilizer may supply the drug or the electromagnetic waves to the specimen housing space. According to such a configuration, since the range of a target space where the sterilization process is supposed to be performed is determined, a more reliable sterilization process is possible. Further, a probability that bacteria and the like enter from outside can be reduced by the chamber.

In this case, for example, at least a part of the wall surface of the chamber may serve as a transparent window having light permeability and the imager may image the specimen held in the specimen container housed in the specimen housing space through the transparent window from the outside of the specimen housing space. In such a configuration, since the imager can be installed outside the specimen housing space, the contamination of the specimen caused by the imager is prevented. Further, since the imager is not required to meet a special requirement such as chemical resistance, apparatus cost can be suppressed low.

For example, the sterilizer may include an electromagnetic wave irradiator provided outside the specimen housing space and configured to irradiate electromagnetic waves to the specimen housing space through the transparent window. By doing so, a configuration for performing the sterilization process needs not be provided in the specimen housing space or loaded into and unloaded from the specimen housing space and the specimen housing space can be maintained cleaner. In this way, the contamination of the specimen can be more reliably prevented.

For example, the sterilizer may supply gas or liquid having a sterilization effect as the drug into the specimen housing space and a discharger may be further provided which discharges the drug supplied to the specimen housing space. In such a configuration, an impact of the drug on a specimen used in later imaging is prevented by preventing the drug from remaining in the specimen housing space after the sterilization process.

For example, a positive pressure application unit for applying a positive pressure relative to outside atmosphere into the specimen housing space may be further provided. By doing so, the generation of an airstream from the outside to the inside of the specimen housing space can be suppressed and the entrance of bacteria and the like contained in outside atmosphere into the specimen housing space can be effectively prevented.

Further, the imaging apparatus according to this invention may further comprise, for example, a specimen storage including an internal space linking to the specimen housing space and maintained in a predetermined temperature/humidity environment and being configured to store the specimen container in the internal space, a gate member for opening and closing between the internal space of the specimen storage and the specimen housing space, and a conveyor for conveying the specimen container between the internal space of the specimen storage and the specimen housing space. In such a configuration, so-called time lapse imaging in which the same specimen is imaged at time intervals can be performed without the specimen being exposed to outside atmosphere.

Further, in the invention, the controller may, for example, make the content of the sterilization process different depending on the specimen. The imaging apparatus of this type can be used to image various biological specimens as objects, but an effective sterilization method differs depending on the types of specimens. By making the content of the sterilization process different depending on the specimen, the contamination of the specimen can be prevented by more reliably sterilizing the holder.

In this case, for example, the controller may determine the content of the sterilization process according to the specimen used in the last imaging. Since the specimen used in the already performed imaging is known, even if substances separated from the specimen adhere to the holder, an impact of the separated substances on the subsequent imaging can be prevented by performing the sterilization process with a process content corresponding to the specimen. Even if the substances separated from the specimen are cells, bacteria or the like, the proliferation thereof in the apparatus can be prevented.

In these cases, for example, the controller may determine the content of the sterilization process based on information on the specimen recorded on the specimen container. Technologies such as writing of characters, a symbol or a bar code on the container and attachment of an IC tag recorded with information have been proposed as a technology of this type to attach information to the specimen container. By determining the content of the sterilization process utilizing such information, a suitable sterilization process corresponding to the content of the specimen can be performed.

For example, in the above invention, the sterilizer may supply both the drug and the electromagnetic waves to the holder. In this case, the drug and the electromagnetic waves may be simultaneously supplied or these may be selectively supplied. By doing so, a more reliable sterilization effect can be obtained against various contamination-causing substances. For example, a substance having an effect as the drug may be generated in a specimen housing space. According to such a configuration, it is not necessary to introduce the drug from the outside of the apparatus and there is no need for a configuration for introducing the drug into the apparatus and drug management cost.

This invention is preferably applied to an imaging apparatus for imaging a biological specimen containing cells or the like and particularly notably effective in preventing the contamination of specimens, particularly, in an apparatus for imaging a plurality of different specimens while replacing them one after another.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

What is claimed is:

1. An imaging apparatus, comprising:
a holder that holds a specimen container carrying a biological specimen;
an imager that images the biological specimen in the specimen container;
a sterilizer that supplies a drug or electromagnetic waves having a sterilization effect to the holder; and
a controller that performs a sterilization process of supplying the drug or the electromagnetic waves to the holder by controlling the sterilizer at least either before or after imaging the biological specimen by the imager;
a chamber that forms a specimen housing space capable of housing the specimen container, wherein the holder is provided in the specimen housing space and the sterilizer supplies the drug or the electromagnetic waves to the specimen housing space; and
a positive pressure application unit that applies a positive pressure relative to outside atmosphere into the specimen housing space.

2. The imaging apparatus according to claim 1, wherein at least a part of a wall surface of the chamber serves as a transparent window having light permeability and the imager images the biological specimen held in the specimen container housed in the specimen housing space through the transparent window from outside of the specimen housing space.

3. The imaging apparatus according to claim 2, wherein the sterilizer includes an electromagnetic wave irradiator provided outside the specimen housing space and configured to irradiate electromagnetic waves to the specimen housing space through the transparent window.

4. The imaging apparatus according to claim 1, wherein the sterilizer supplies gas or liquid having a sterilization effect as the drug into the specimen housing space and a discharger is further provided which discharges the drug supplied to the specimen housing space.

5. An imaging apparatus, comprising:
a holder that holds a specimen container carrying a biological specimen;
an imager that images the biological specimen in the specimen container;
a sterilizer that supplies a drug or electromagnetic waves having a sterilization effect to the holder; and a controller that performs a sterilization process of supplying the drug or the electromagnetic waves to the holder by controlling the sterilizer at least either before or after imaging the biological specimen by the imager;

a chamber that forms a specimen housing space capable of housing the specimen container, wherein the holder is provided in the specimen housing space and the sterilizer supplies the drug or the electromagnetic waves to the specimen housing space;

a specimen storage that includes an internal space linking to the specimen housing space and maintained in a predetermined temperature and humidity environment and that stores the specimen container in the internal space;

a gate member that opens and closes between the internal space of the specimen storage and the specimen housing space; and a conveyor that conveys the specimen container between the internal space of the specimen storage and the specimen housing space.

6. The imaging apparatus according to claim 5, wherein at least a part of a wall surface of the chamber serves as a transparent window having light permeability and the imager images the biological specimen held in the specimen container housed in the specimen housing space through the transparent window from outside of the specimen housing space.

7. The imaging apparatus according to claim 6, wherein the sterilizer includes an electromagnetic wave irradiator provided outside the specimen housing space and configured to irradiate electromagnetic waves to the specimen housing space through the transparent window.

8. The imaging apparatus according to claim 5, wherein the sterilizer supplies gas or liquid having a sterilization effect as the drug into the specimen housing space and a discharger is further provided which discharges the drug supplied to the specimen housing space.

* * * * *